US007978822B2

(12) United States Patent
Windt

(10) Patent No.: US 7,978,822 B2
(45) Date of Patent: Jul. 12, 2011

(54) MIRROR MOUNTING, ALIGNMENT, AND SCANNING MECHANISM AND SCANNING METHOD FOR RADIOGRAPHIC X-RAY IMAGING, AND X-RAY IMAGING DEVICE HAVING SAME

(75) Inventor: David L. Windt, New York, NY (US)

(73) Assignee: Reflective X-Ray Optics LLC, New York, NY (US)

(*) Notice: Subject to any disclaimer, the term of this patent is extended or adjusted under 35 U.S.C. 154(b) by 97 days.

(21) Appl. No.: 12/362,937

(22) Filed: Jan. 30, 2009

(65) Prior Publication Data
US 2009/0190720 A1 Jul. 30, 2009

Related U.S. Application Data

(60) Provisional application No. 61/062,918, filed on Jan. 30, 2008.

(51) Int. Cl.
*G21K 1/06* (2006.01)
*G02B 5/08* (2006.01)
*G02B 7/182* (2006.01)

(52) U.S. Cl. ............. 378/84; 378/85; 359/850; 359/871

(58) Field of Classification Search .................... 378/84, 378/85, 146; 359/196.1, 203.1, 346, 838, 359/850–853, 855–859, 862–869, 871–884
See application file for complete search history.

(56) References Cited

U.S. PATENT DOCUMENTS

| 4,969,175 | A | * | 11/1990 | Nelson et al. | ................. | 378/146 |
| 5,182,763 | A | | 1/1993 | Iizuka et al. | | |
| 5,737,137 | A | * | 4/1998 | Cohen et al. | .................. | 359/859 |
| 6,278,764 | B1 | * | 8/2001 | Barbee et al. | .................... | 378/84 |
| 6,917,667 | B2 | * | 7/2005 | Fujinawa et al. | ............... | 378/70 |
| 7,511,902 | B2 | * | 3/2009 | Wings et al. | .................... | 359/822 |
| 2001/0021239 | A1 | * | 9/2001 | Itoga et al. | ....................... | 378/34 |
| 2002/0080916 | A1 | | 6/2002 | Jiang et al. | | |
| 2003/0174303 | A1 | * | 9/2003 | Naulleau | .......................... | 355/71 |
| 2004/0066903 | A1 | * | 4/2004 | Fujinawa et al. | ............. | 378/145 |
| 2008/0013685 | A1 | * | 1/2008 | Iwasaki et al. | .................. | 378/86 |

OTHER PUBLICATIONS

International Search Report and Written Opinion for PCT/US2009/032646, dated Sep. 1, 2009.
Schnopper et al., X-ray monochromator for divergent beam radiography using conventional and laser produced X-ray sources, 2001 Proceedings of SPIE vol. 4502 pp. 19-29.
Harms et al., Thin film multilayer x-ray monochromator, 2001 Proceedings of SPIE vol. 4501 pp. 193-200.

* cited by examiner

*Primary Examiner* — Anastasia Midkiff
(74) *Attorney, Agent, or Firm* — Pryor Cashman LLP; Barry E. Negrin, Esq.

(57) ABSTRACT

An X-ray imaging device and alignment/scanning system include at least one multilayer X-ray mirror mounted on a multi-axis adjustable mirror mount pivotable about a scanning axis. A mirror scanner is coupled with the mirror mount and synchronized with the X-ray source so that the mirror scanner moves the mirror mount about the scanning axis. The invention may include a plurality of mirrors, optionally in a stack, and preferably including first and second mirrors respectively adapted to reflect X-rays of first and second energies. A movable attenuation plate having a window selectively allows X-rays to be transmitted by one of the mirrors and blocks X-rays from the other mirror(s). Sets of the mirrors may be configured in blocks or interspersed. The mirror scanner may be operable at variable speeds to enable selective control of the scanning speed of the mirror.

33 Claims, 16 Drawing Sheets

Top View

MIRROR MOUNTING, ALIGNMENT, AND SCANNING MECHANISM AND SCANNING METHOD FOR RADIOGRAPHIC X-RAY IMAGING, AND X-RAY IMAGING DEVICE HAVING SAME

RELATED APPLICATIONS

Domestic priority is claimed from U.S. Provisional Patent Application No. 61/062,918, filed Jan. 30, 2008, entitled "Mirror Mounting, Alignment, and Scanning Mechanism, and Scanning Method, for Radiographic X-ray Imaging", the entirety of which is incorporated by reference herein.

BACKGROUND OF THE INVENTION

1. Field of the Invention

The invention is directed to imaging systems, and more particularly to radiographic X-ray imaging systems, for medical, industrial, and other applications.

2. Description of Related Art

Radiographic X-ray imaging systems for medical, industrial and other applications typically use a point-source X-ray tube in which energetic electrons impinge upon a solid metal target thereby producing a cone-beam of X-ray light emanating from the focal spot. The spectrum of X-rays emitted from such tubes is poly-energetic, having line emission characteristic of the anode material used in the tube (commonly tungsten, or in the case of mammography, molybdenum or rhodium) superimposed on a broad continuum of Bremsstrahlung radiation extending to a high-energy cutoff determined by the applied voltage. For many imaging tasks, however, increased image contrast—and lower patient dose, in the case of medical applications—can be achieved using mono-energetic radiation.

One method for producing (nearly) mono-energetic radiation from electron-impact X-ray tubes (or other point-sources of X-rays) utilizes multilayer X-ray mirrors to reflect and filter the X-ray light before it reaches the tissue or sample under study. [See, for example, 'X-ray monochromator for divergent beam radiography using conventional and laser produced X-ray sources', H. W. Schnopper, S. Romaine, and A. Krol, Proc. SPIE, 4502, 24, (2001)]. The X-ray mirrors include flat substrates coated with X-ray-reflective multilayer coatings that reflect X-rays only over a narrow energy band. The multilayer X-ray mirrors are positioned between the X-ray tube focal spot and the sample or patient. Because the mirrors only work at shallow grazing incidence angles, a single mirror will only yield a thin fan-beam of mono-energetic X-ray light. Thus, to produce mono-energetic light over a large field at the image plane, one of two approaches can be used. In the first approach, a single mirror is scanned over a wide angular range during the X-ray exposure. In the second approach, an array of stacked mirrors are used, constructed from a number of thin mirrors and spacers that are stacked together with high precision in a wedge shape: while each individual mirror will produce a narrow fan beam, the array of mirrors will collectively produce an array of co-aligned fan beams. In the second approach using a mirror stack, however, the illumination pattern will also include dark strips corresponding to the regions where the X-ray light is blocked by the edges of the mirrors. To compensate for the dark strips, the mirror stack can be scanned during exposure, similar to the way in which a single mirror is scanned in the first approach (albeit over a much smaller angular range), so that the bright and dark strips are averaged together to produce uniform illumination.

In any case, the requirements on positioning the mirrors relative to the focal spot are stringent: in particular, the angular position of each mirror must be such that the incidence angle of X-rays is controlled to a fraction of a degree. As an example, in the specific case of multilayer X-ray mirrors designed for mammography systems operating near 20 keV, approximately, typical grazing incidence angles are in the range of 0.3-0.7 degrees, while the angular acceptance angle of the narrow-band multilayer coating can be as small as 0.02 degrees; therefore the mirror must be positioned so that the error in graze angle is perhaps half of the acceptance angle, i.e., 0.01 degrees, or less. For other types of X-ray imaging systems utilizing higher-energy X-rays, the graze angles and acceptance angles are even smaller, and thus the requirements on alignment are even more stringent than for mammography.

For either approach using X-ray mirrors just described, i.e., using a single mirror or a mirror stack, a precision scanning mechanism is required for illumination over a large field. Such a scanning mechanism must be constructed such that the alignment of the mirror or mirror stack relative to the X-ray focal spot is precisely maintained during the course of the scan, the scan range must be accurately controlled (i.e., to a small fraction of a degree), and the scanning mechanism must be highly repeatable so that no exposure errors are introduced. The scanning mechanism must be constructed so that the rotation axis can be made to coincide with the focal spot with a precision that is determined by the size of the focal spot and by the angular acceptance of the multilayer mirrors. For mammography, for example, the displacement error between the rotation axis and the focal spot must be smaller than 0.05 mm, approximately. For other imaging applications, this displacement error may be larger or smaller.

In summary, while the notion of using multilayer X-ray mirrors in conjunction with point-source X-ray sources to produce mono-energetic X-rays for radiographic imaging has been described previously, no mechanism has yet been developed to accurately and precisely mount, align, and scan the mirrors.

SUMMARY OF THE INVENTION

The present invention includes a mounting, alignment, and scanning mechanism for grazing incidence X-ray mirrors used in conjunction with point-source X-ray tube. The invention includes (a) a 5-axis adjustable mirror mount, (b) a computer-controlled mirror scanner that is synchronized with the X-ray generator, (c) a two-axis adjustment mechanism for precisely positioning the scan axis relative to the X-ray focal spot, (d) a moving entrance grid that can be precisely positioned relative to an X-ray mirror stack in order to select which mirrors are used for an individual X-ray exposure, and (e) a scanning anti-scatter grid, having an attenuating slotted plate that is matched to the illumination pattern as defined by the specific mirror configuration. The scanning anti-scatter grid is used to minimize scattering in one direction. The present invention is aimed specifically at mammographic applications, however it can apply equally well to all other medical and industrial radiographic X-ray imaging applications.

In one embodiment, the invention is a multilayer X-ray mirror alignment and scanning system for X-ray imaging devices utilizing a point-source X-ray tube having a focal spot. The alignment and scanning system includes a multi-axis adjustable mirror mount upon which at least one multilayer X-ray mirror is mounted. The mirror mount is pivotable about a scanning axis alignable with the focal spot. A computer-controlled mirror scanner is coupled with the mirror mount and synchronized in operation with the point-source X-ray tube. When the point-source X-ray tube is operated, the mirror scanner rotates the mirror mount about the scanning axis. The mirror mount is preferably attached to an optics bracket pivotably mounted with respect to the focal spot. The mirror scanner preferably includes a linear motor drive that applies force against the optics bracket and thus causes the optics bracket and the mirror mount to rotate about the scanning axis while remaining aligned with the focal spot. Preferably, the mirror mount further includes a 5-axis optic positioner having three orthogonal translations and two orthogonal rotations, adapted to enable positioning of the mirror relative to the X-ray focal spot and scanning axis. A two-axis adjustment mechanism is also preferably provided adapted to position the scanning axis of the mirror mount relative to the X-ray focal spot.

In a preferred embodiment, the at least one multilayer X-ray mirror includes a plurality of multilayer mirrors rigidly secured to one another in a mirror stack, which more preferably includes a first set or plurality of multilayer mirrors adapted to reflect X-rays of a first energy and a second set or plurality of multilayer mirrors adapted to reflect X-rays of a second energy. More than two sets of mirrors (e.g., three or more sets) may be provided, each adapted to reflect X-rays of different respective energies. In this preferred embodiment, a movable attenuation plate having at least one window is disposed either one of i) interposed between the X-ray tube and the mirror stack or ii) interposed between the mirror stack and the item to be imaged, the window selectively allowing at least one of the pluralities of mirrors to transmit X-rays of at least one corresponding energy to the item to be imaged, and the rest of the attenuation plate blocking at least another of the pluralities of mirrors from transmitting X-rays of at least one different corresponding energy. In this way, by selectively blocking some of the mirrors in the stack and simultaneously allowing X-rays to reflect from other mirrors in the stack to the item to be imaged, one thereby selects an X-ray energy (or plural energies) to be transmitted for imaging.

The multiple sets or pluralities of mirrors in a mirror stack may be arranged in different ways. For example, the first plurality of mirrors can be provided substantially all adjacent one another in a first block with the second plurality of mirrors being provided substantially all adjacent one another in a second block. In this configuration, the window of the attenuation plate would be an aperture dimensioned to allow X-rays to be transmitted to/from one of the blocks of mirrors while shielding the other block(s). Alternatively, the first and second pluralities of mirrors can be interspersed with one another. In such a configuration, the window of the attenuation plate includes a plurality of slots dimensioned to allow X-rays to be reflected from one of the pluralities of mirrors to the item to be imaged while shielding the other of the pluralities of mirrors.

The inventive alignment and scanning system may also include a scanning anti-scatter grid, disposed between the item to be imaged and the X-ray sensor (either film or digital), having an attenuating slotted plate matched to an illumination pattern created by the at least one X-ray mirror.

Optionally, the mirror scanner may be operable at a selectively variable speed to thereby enable selective control of the scanning speed of the mirror. By controlling both the scanning speed of the mirror (e.g., the rate at which the linear motor drive pushes the optics bracket) and the position of the entrance grid aperture, the invention provides unrestricted control over X-ray intensity and energy, respectively, as a function of position in the image plane.

Another aspect of the invention is an X-ray imaging device. The inventive device includes a point-source X-ray tube having a focal spot and at least one multilayer X-ray mirror mounted on a multi-axis adjustable mirror mount. The mirror mount is pivotable about a scanning axis alignable with the focal spot. A computer-controlled mirror scanner is coupled with the mirror mount and synchronized in operation with the point-source X-ray tube. When the point-source X-ray tube is operated, the mirror scanner moves the mirror mount about the scanning axis. The mirror scanner preferably includes a linear motor drive applying force against the mirror mount to rotate the mirror mount about the scanning axis while keeping the scanning axis aligned with the X-ray focal spot.

As above, the at least one multilayer X-ray mirror may include a plurality of multilayer mirrors rigidly secured to one another in a mirror stack, and the stack may preferably include a first set or plurality of multilayer mirrors adapted to reflect X-rays of a first energy and a second set or plurality of multilayer mirrors adapted to reflect X-rays of a second energy. A movable attenuation plate having at least one window is provided, disposed either one of i) interposed between the X-ray tube and the mirror stack or ii) interposed between the mirror stack and the item to be imaged. The window selectively allows at least one of the pluralities of mirrors to transmit X-rays of at least one corresponding energy to the item to be imaged, and the rest of the attenuation plate blocks at least another of the pluralities of mirrors from transmitting X-rays of at least one different corresponding energy, thereby enabling selection of at least one X-ray energy to be transmitted for imaging. The sets of mirrors may be configured in homogeneous blocks, in which case the window of the attenuation plate includes an aperture dimensioned to allow transmission of X-rays to/from one of the blocks while shielding the other of the blocks. Alternatively, the first and second pluralities of mirrors are interspersed with one another; in that case, the attenuation plate window includes a plurality of slots dimensioned to allow transmission of X-rays to/from one (or more) of the pluralities of mirrors while shielding the other of the pluralities of mirrors.

The inventive X-ray imaging device may optionally allow the mirror scanner to be operable at a selectively variable speed to thereby enable selective control of the scanning speed of the mirror. A slower scanning speed over a specific region of the item to be imaged corresponds to a greater exposure of X-rays in that region, while a faster scanning speed corresponds to a lesser exposure of X-rays. By controlling the X-ray exposure as a function of position, the image quality can be optimized, and in the case of medical imaging the patient dose can be minimized, for each specific item to be imaged.

In another aspect of the invention, the invention is an X-ray imaging device having a point-source X-ray tube which has a focal spot. A plurality of multilayer X-ray mirrors are rigidly secured to one another in a mirror stack, the mirror stack including a first plurality of multilayer mirrors adapted to reflect X-rays of a first energy and a second plurality of multilayer mirrors adapted to reflect X-rays of a second energy. A scannable mirror mount is provided upon which the mirror stack is mounted, the mirror mount alignable with the focal spot. A movable attenuation plate having at least one window is provided, disposed either one of i) interposed between the X-ray tube and the mirror stack or ii) interposed between the mirror stack and the item to be imaged. The window selectively allows at least one of the pluralities of mirrors to transmit X-rays of at least one corresponding energy to the item to be imaged, and the rest of the attenuation plate blocks at least another of the pluralities of mirrors from transmitting X-rays of at least one different corresponding energy, thereby enabling selection of at least one X-ray energy to be transmitted for imaging.

The first plurality of mirrors may be all adjacent one another in a first block with the second plurality of mirrors being substantially all adjacent one another in a second block. The attenuation plate window in this configuration includes an aperture dimensioned to allow X-rays to be transmitted by at least one of the blocks while shielding at least another of the blocks (preferably allowing transmission of X-rays from one block and blocking transmission of X-rays from all other blocks). Alternatively, the first and second pluralities of mirrors are interspersed with one another; the window of the attenuation plate in this configuration includes a plurality of slots dimensioned to allow transmission of X-rays to/from one of the pluralities of mirrors while shielding the other of the pluralities of mirrors.

In this X-ray imaging device in accordance with the invention, the mirror mount is preferably pivotable about a scanning axis alignable with the focal spot, the X-ray imaging device further including a computer-controlled mirror scanner, coupled with the mirror mount and synchronized in operation with the point-source X-ray tube. When the point-source X-ray tube is operated, the mirror scanner moves the mirror mount about the scanning axis. The mirror scanner is preferably operable at a selectively variable speed to thereby enable selective control of the scanning speed of the mirror.

Another aspect of the invention includes a method of performing X-ray imaging utilizing substantially mono-energetic X-rays. A plurality of multilayer X-ray mirrors are provided rigidly secured to one another in a mirror stack, the mirror stack including a first plurality of multilayer mirrors adapted to reflect X-rays of a first energy and a second plurality of multilayer mirrors adapted to reflect X-rays of a second energy. X-rays from an X-ray source are selectively allowed to strike one of the pluralities of mirrors while blocking X-rays from the other of the pluralities of mirrors, thereby selecting an X-ray energy to be transmitted for imaging. Preferably, the selectively allowing step further includes the steps of providing a movable attenuation plate having at least one window either between the X-ray tube and the mirror stack or between the mirror stack and the item to be imaged, and selectively moving the attenuation plate so as to align the window with the desired of the pluralities of X-ray mirrors.

The mirror stack is preferably mounted on a mirror mount pivotable about a scanning axis alignable with a focal spot of the X-ray source. In this case, the inventive method includes the step of rotating the mirror mount about the scanning axis while maintaining alignment of the scanning axis with the X-ray focal spot. Optionally, the inventive method further includes the step of varying the speed of rotation of the mirror mount about the scanning axis to thereby enable selective control of the scanning speed of the mirror. By utilizing the speed varying step and the attenuation plate moving step, the inventive method enables control of X-ray intensity and energy-, respectively, as a function of position with respect to an item to be imaged.

BRIEF DESCRIPTION OF THE DRAWINGS

FIG. 1 is a schematic diagram showing the use of planar, multilayer X-ray mirrors in conjunction with a conventional point-source X-ray tube for mono-energetic imaging.

FIG. 6 shows examples of multi-energy mirror stacks and translatable entrance grids and scanning anti-scatter grids in accordance with the invention.

DETAILED DESCRIPTION OF THE INVENTION

Description of the invention will now be given with reference to FIGS. 2-7. It should be understood that these figures are exemplary in nature and in no way serve to limit the scope of the invention, which is defined by the claims appearing hereinbelow.

A traditional radiographic X-ray imaging system has a point-source X-ray tube and an X-ray-sensitive imaging detector (either film/screen or digital): X-ray photons emitted from the focal spot pass through the tissue or sample under study where they are attenuated by an amount that depends on the composition and density of the sample. The resultant image is thus an attenuation map of the sample, integrated along the direction of X-ray propagation.

Figure 1A:
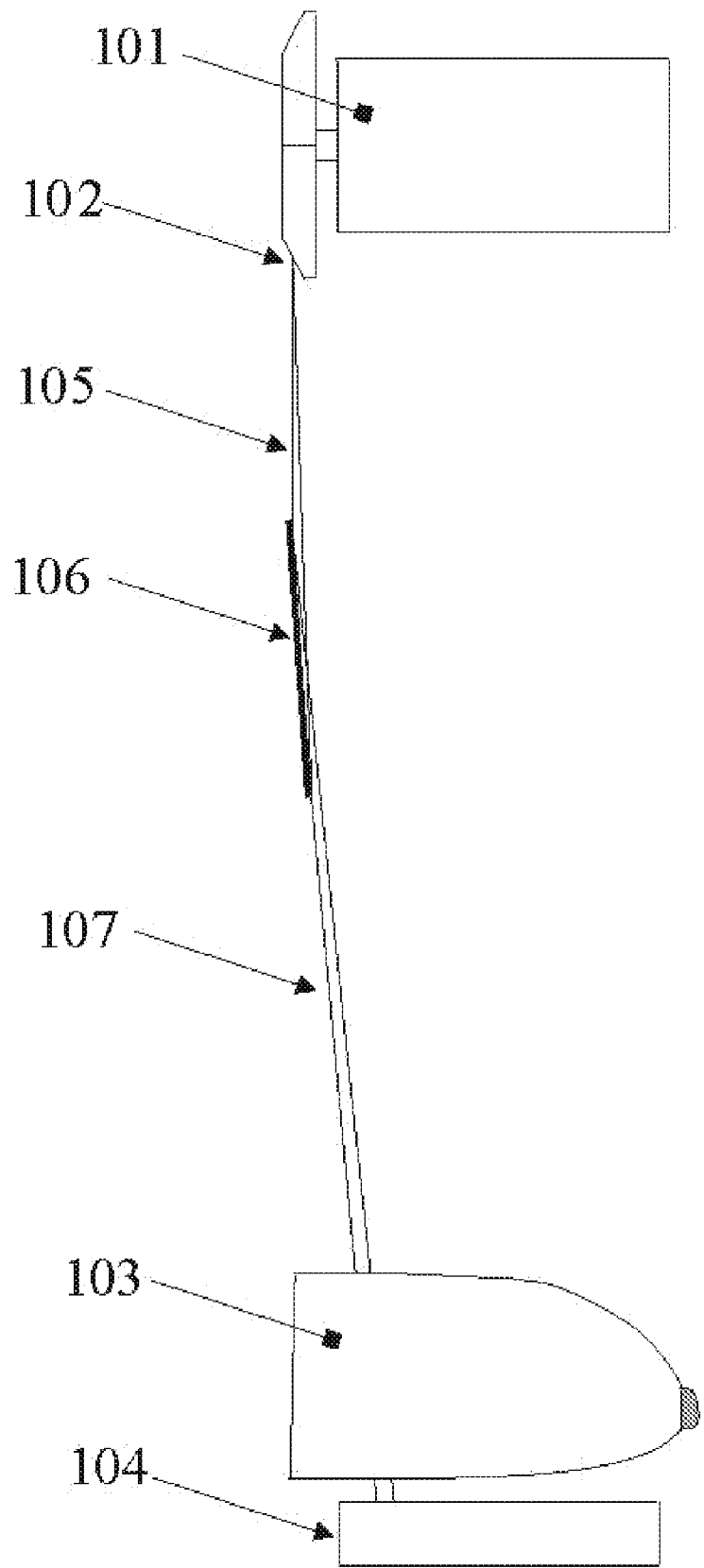
FIG. 1a depicts a single-mirror that yields a single mono-energetic fan-beam.
Figure 1B:
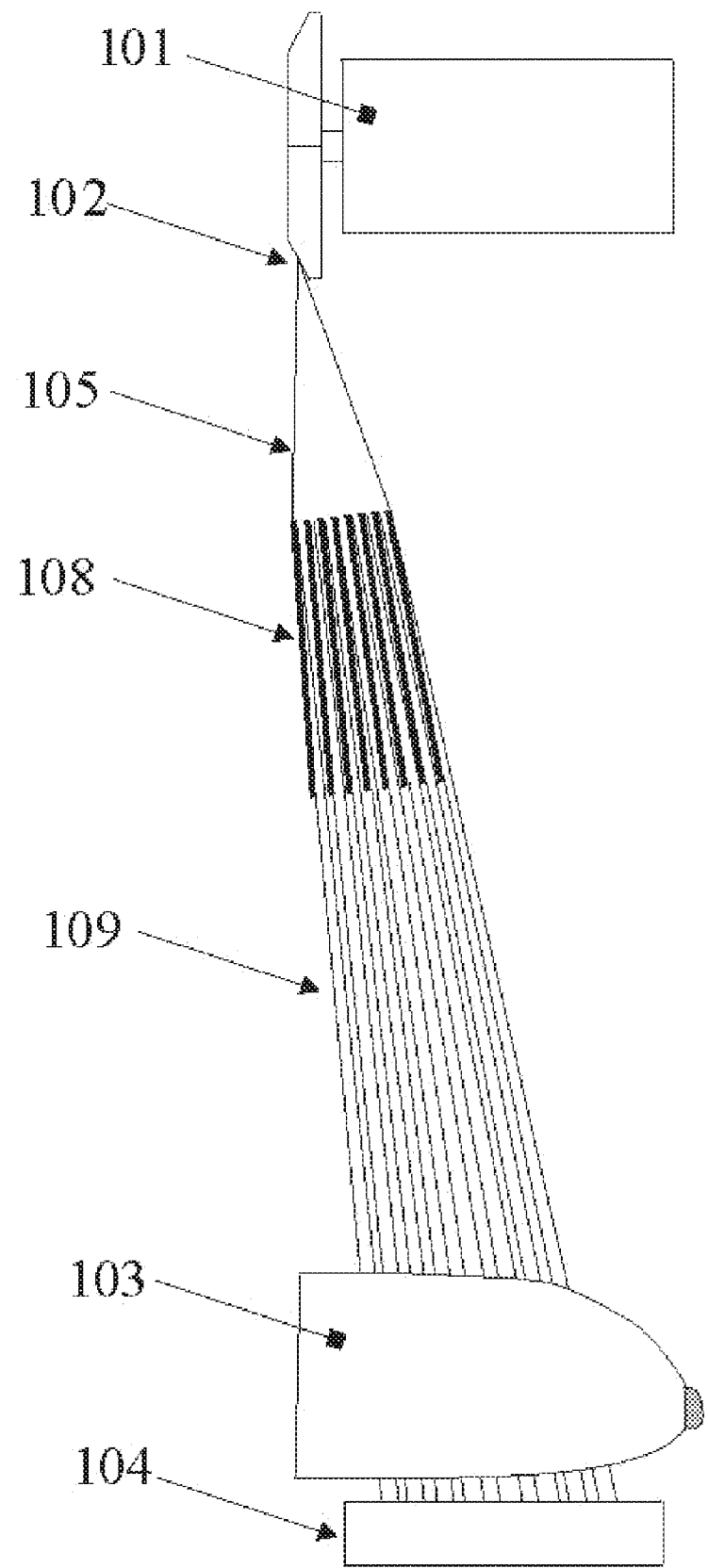
FIG. 1b depicts a mirror stack that yields a co-aligned array of mono-energetic fan-beams.
Figure 2A:
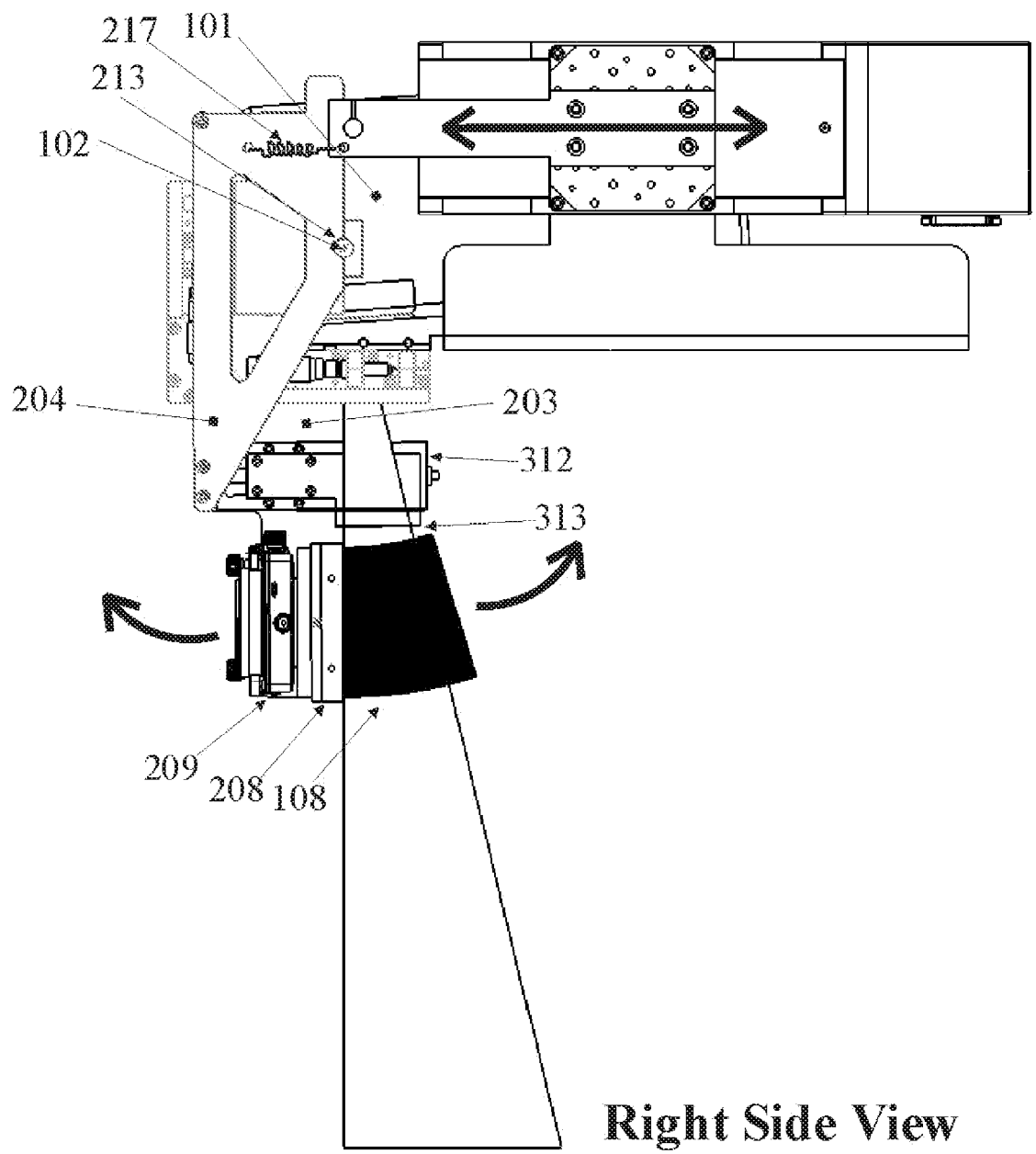
FIG. 2 shows an X-ray mirror stack, a mirror-stack mount with 5-axis of positioning, and a scanning optics bracket assembly and drive system in accordance with the invention, all mounted to a conventional point-source X-ray tube.
Figure 2B:
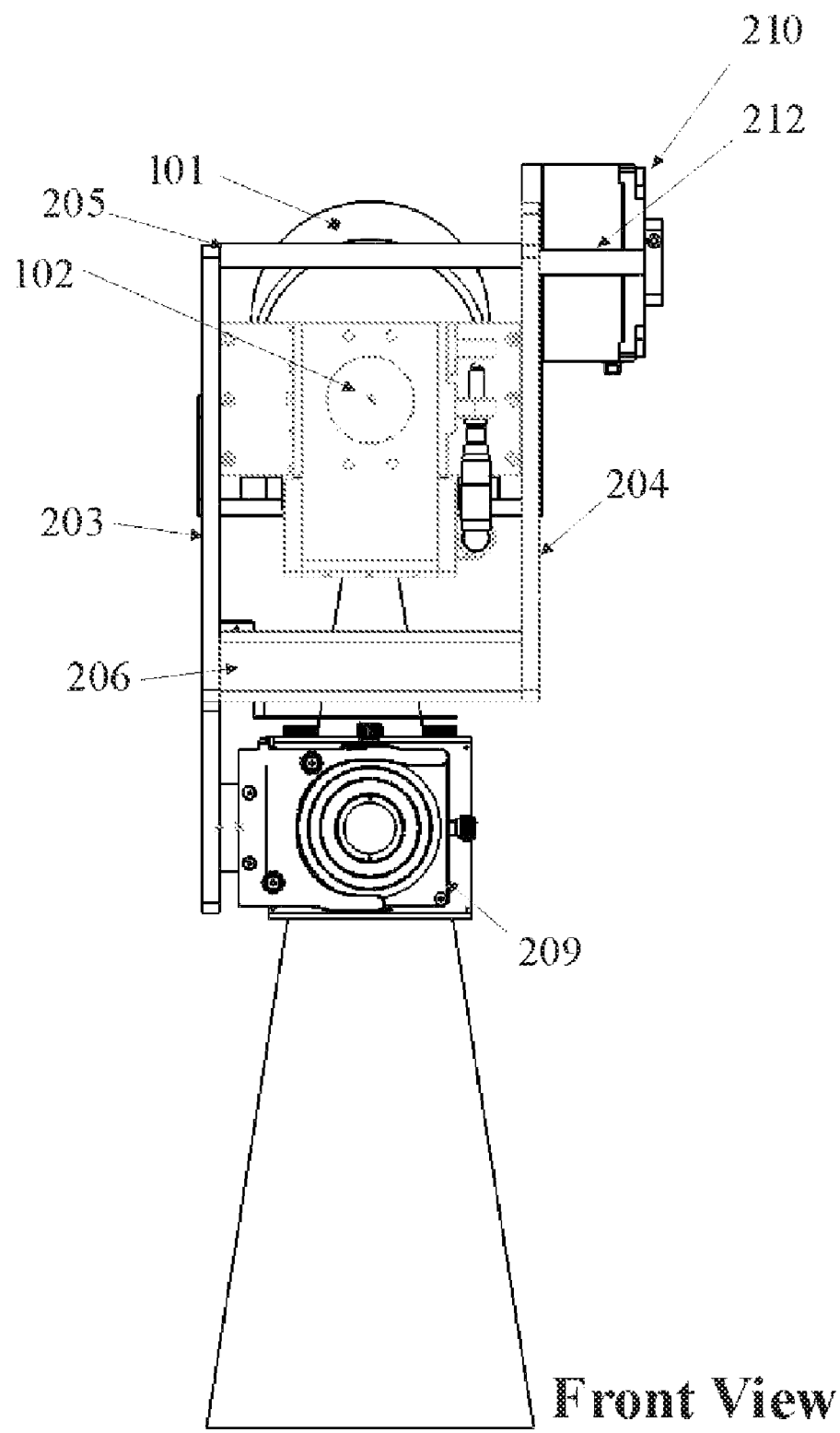
Figure 2C:
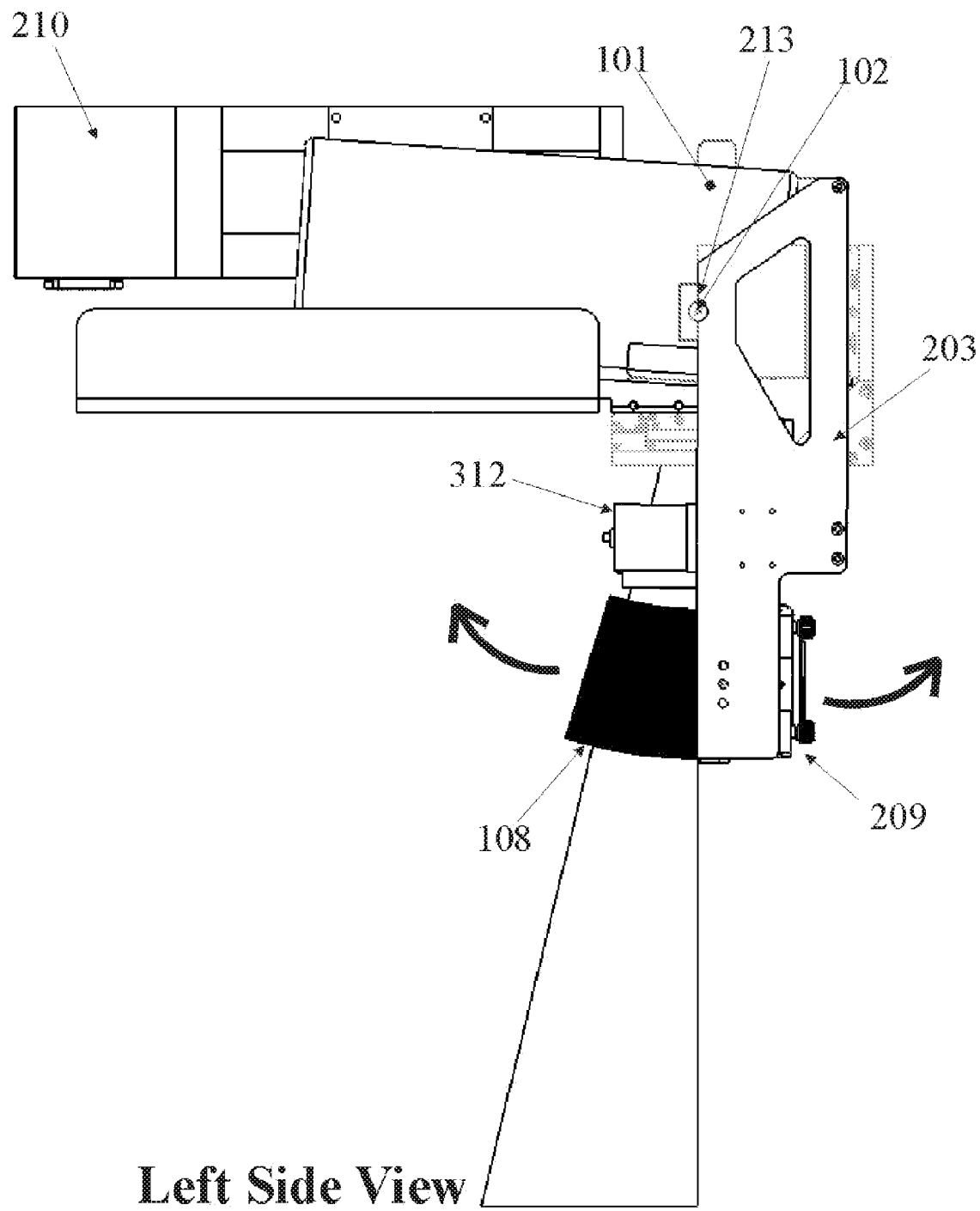
Figure 2D:
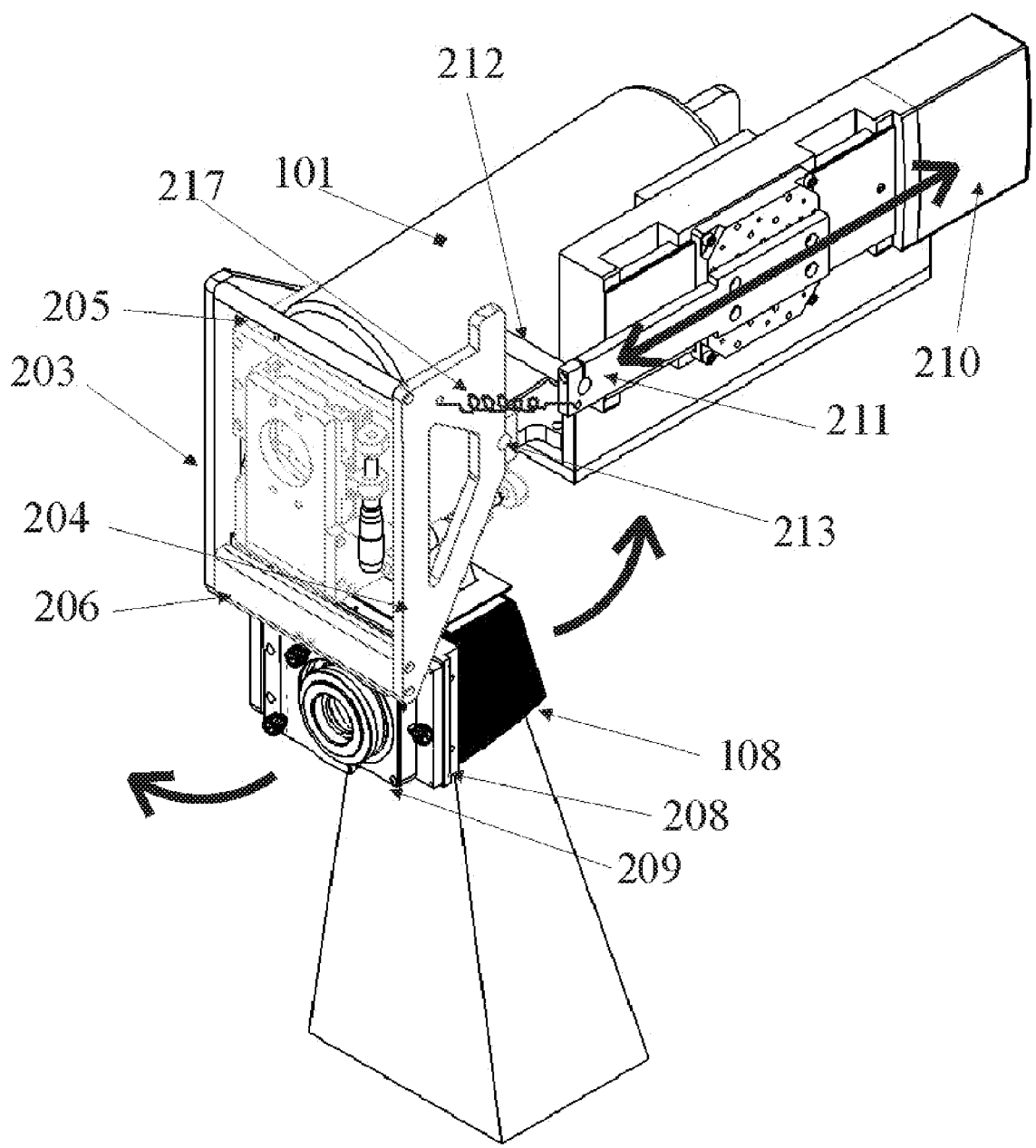
Figure 2E:
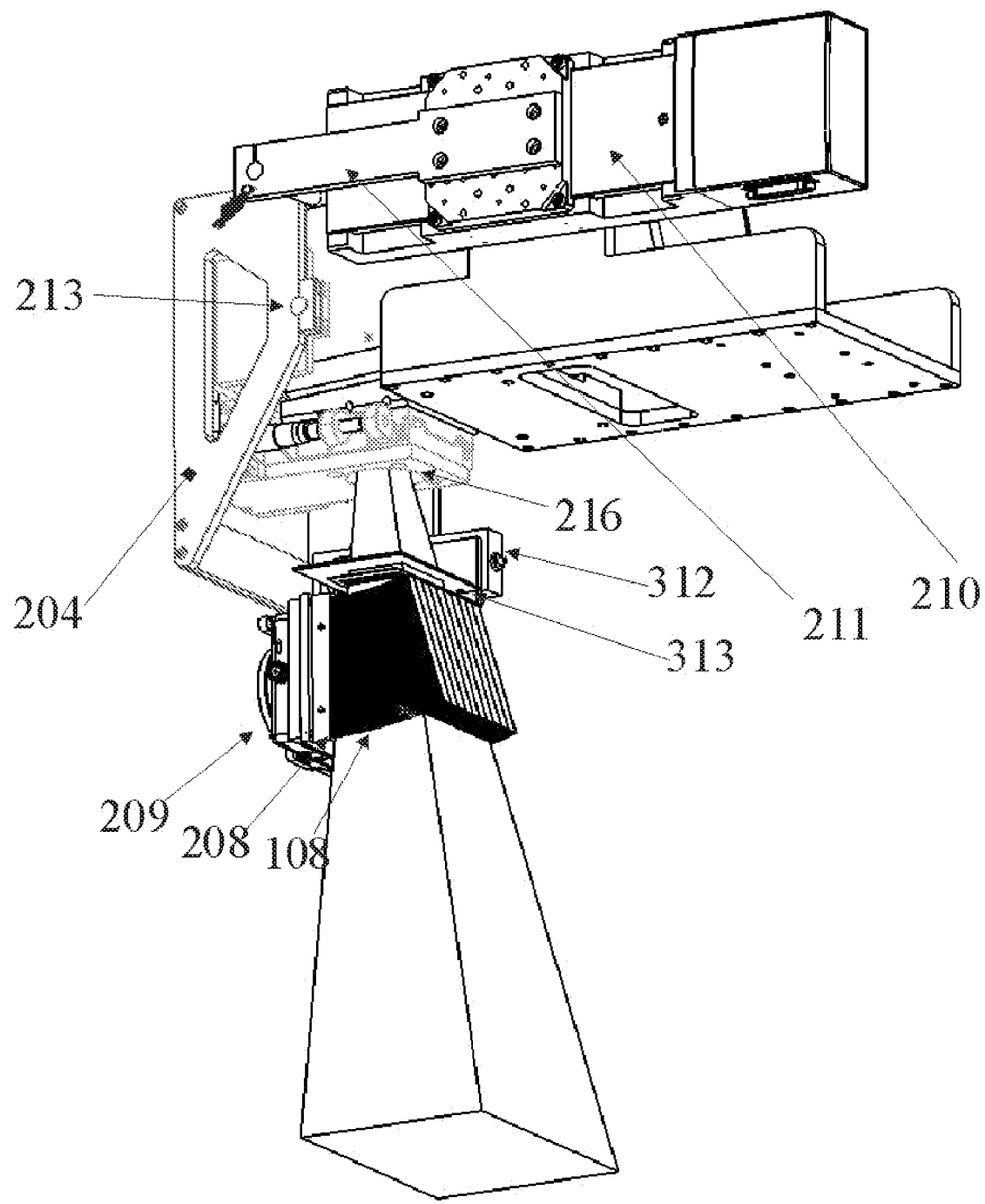
Figure 2F:
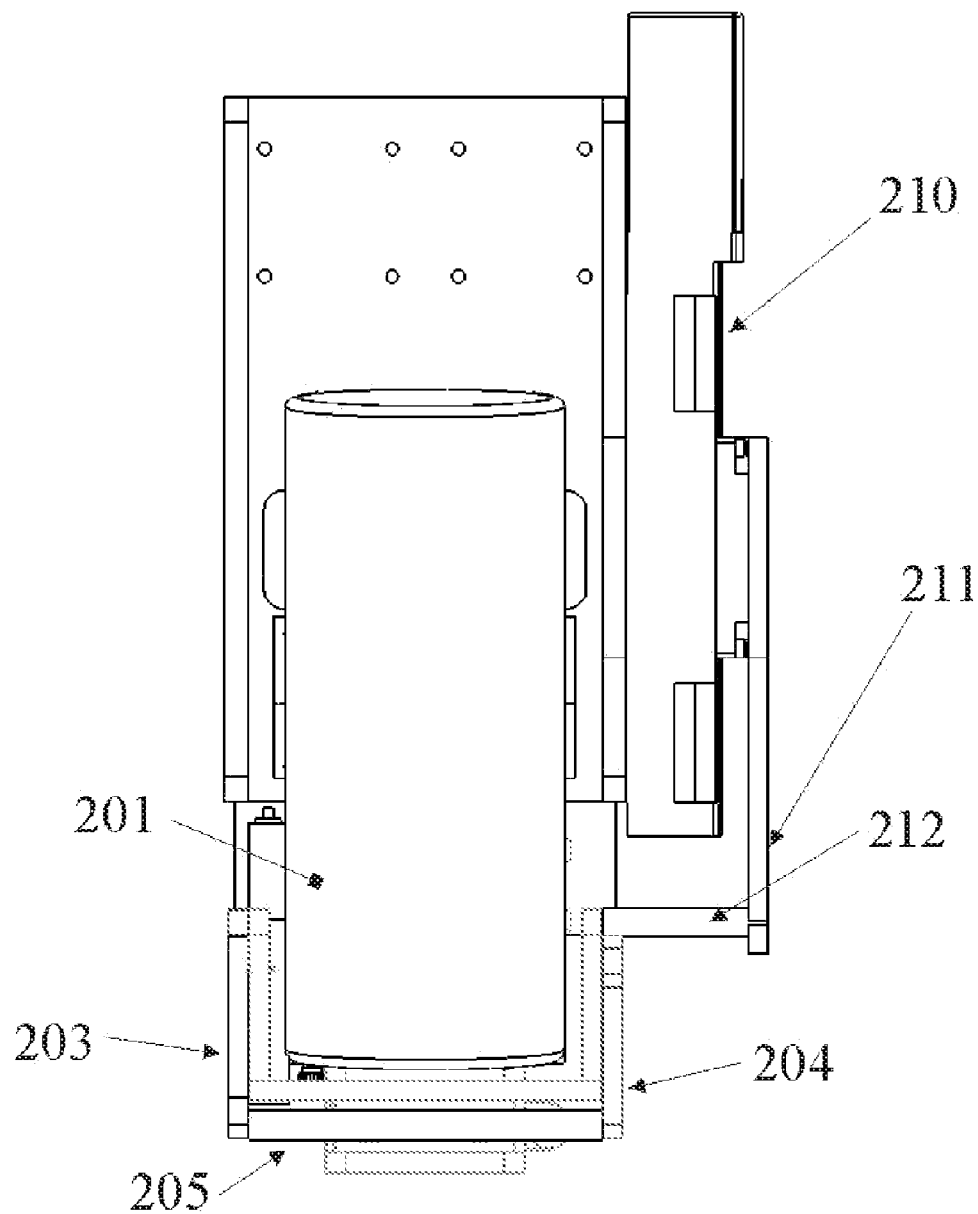
Figure 3:
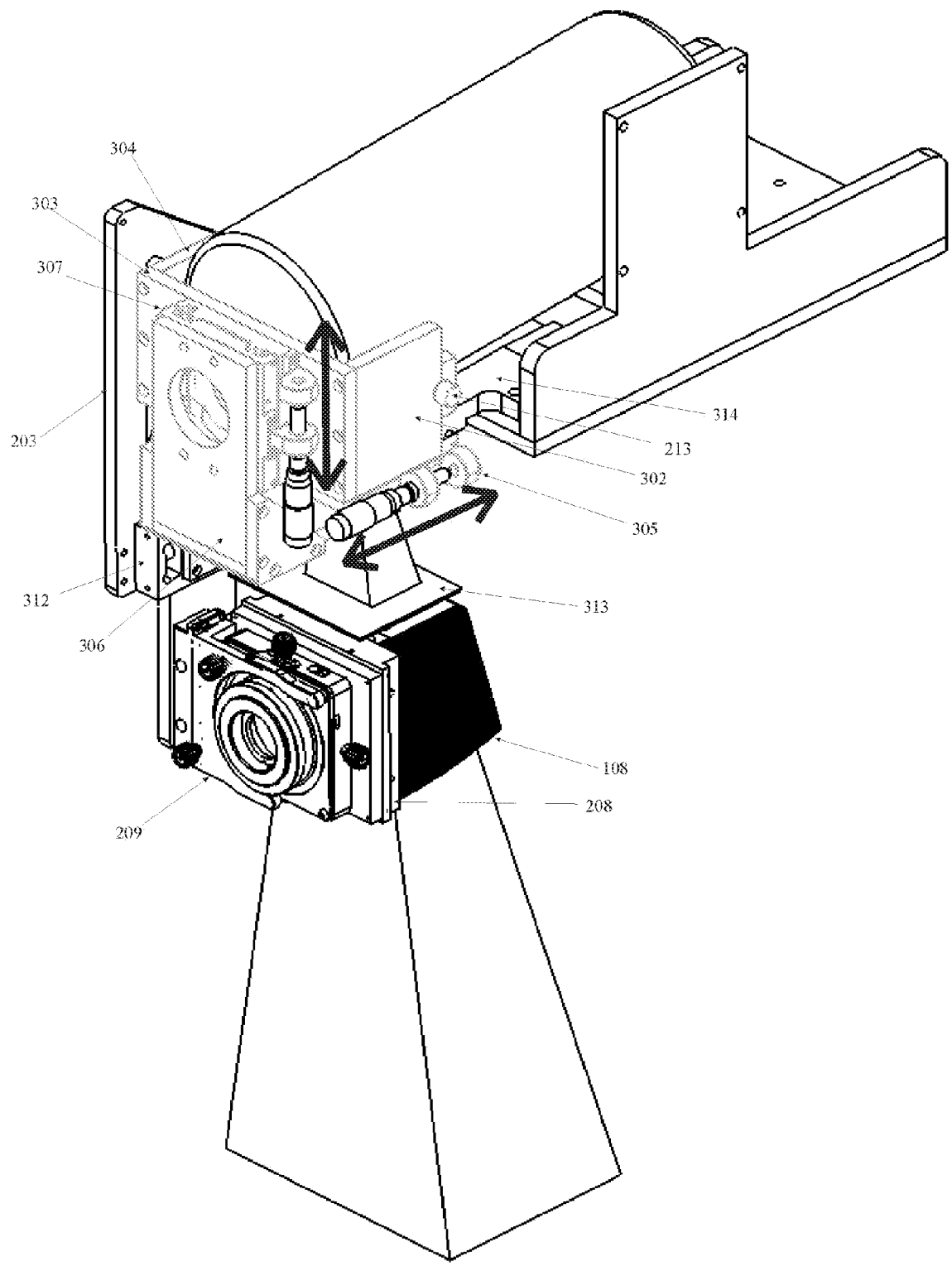
FIG. 3 is a cut-away view of the scanning optics bracket assembly of FIG. 2 and pivot U-bracket assembly that provides a method of positioning the scan axis relative to the X-ray focal spot, in accordance with the invention.

For many applications, increased signal contrast (and lower dose, for medical applications) can be obtained using mono-energetic X-rays, as produced, for example, by graded, periodic multilayer X-ray mirrors. One configuration utilizing X-ray mirrors is shown in FIG. 1a, in which a single mirror (106) is used to produce a mono-energetic fan beam of X-rays (107). Another configuration is shown in FIG. 1b, in which an array of co-aligned X-ray mirrors (108) are used to produce an array of parallel mono-energetic fan beams (109). Both FIGS. 1a and 1b show the X-ray tube (101), X-ray focal (102), tissue under study (103), detector (104), and poly-energetic fan beam (105).

Shown in FIG. 2 is a mechanism in accordance with the invention for mounting and aligning X-ray mirrors rigidly to a conventional mammography X-ray tube (101); the assembly also incorporates a precise scanning mechanism as well. The mounting, aligning and scanning mechanisms shown in FIG. 2 are part of the present invention. The system shown in FIG. 2 depicts an X-ray mirror stack (108), but the concept applies equally well to the case of a single mirror configuration (106).

The X-ray mirror stack includes an array of thin X-ray mirrors and spacers rigidly mounted together into a wedge shape: the mirror stack is designed so that when it is perfectly mounted in the system, the focus of the wedge is coincident with the X-ray tube focal spot (102). The mirror stack is permanently attached to a base-plate (208) that is itself attached to the mounting surface of a 5-axis optic positioner (209) (such as those commercially available from Newport Corp. of Irvine, Calif., e.g., model LP-2A) that provides three orthogonal translations and two orthogonal rotations. The optic positioner (209) (also shown in FIG. 3), which is rigidly attached to the "optics bracket left-side plate" (203), thus provides a mechanism for precise positioning of the mirror or mirror stack relative to the X-ray tube focal spot, along all necessary axes. The actuators and or stages that make up the optic positioner can be of the locking type, so as to prevent errant position adjustments once the mirror has been properly aligned.

The "optics bracket left-side plate" (203) (to which the mirror or mirror stack is mounted) is part of the "optics bracket assembly"; the "optics bracket assembly" also includes the "optics bracket right-side plate" (204) and two cross-braces (205,206) for increased stiffness. The "optics bracket left-side plate" and "optics bracket right-side plate" (also shown in FIG. 3) each include a precision bored hole for attachment to one end of a cylindrical flexural-pivot (213) (such as those commercially available from Riverhawk Co. of New Hartford, N.Y., e.g., model 5016-800.) The other end of each flexural-pivot is attached to the "pivot U-bracket left-side plate" (304) or the "pivot U-bracket right-side plate" (302), respectively, which also include matching precision bored holes to accommodate the flexural pivots. Conventional rotary bearings also could be used in place of the flexural pivots. The "pivot U-bracket assembly" includes the "pivot U-bracket left-side plate" (304), the "pivot U-bracket right-side plate" (302) and the "pivot U-bracket base plate" (303). The "pivot U-bracket base plate" (303) is attached to one side of a linear-translation stage (307) (such as the Newport Corp. model M-426A) oriented for vertical translation; the other side of the translation stage is mounted to an "L-bracket assembly" (306) that is in turn mounted to another linear-translation stage (305) oriented for horizontal translation. The horizontal translation stage, which includes a central aperture to allow the X-ray beam to pass unimpeded (216), is mounted rigidly to the "X-ray tube mounting plate" (314), to which the X-ray tube is also rigidly attached.

The horizontal (305) and vertical (307) translation stages thus provide a precise adjustment mechanism for positioning the left- and right-side flexural pivots (301) simultaneously; this mechanism is therefore used to position the flexural pivot (or bearing) axes to be coincident with the X-ray tube focal spot, with a precision limited, ultimately, by the precision, repeatability and stability of the translation stages. Commercial stages can easily provide precision of 1 micron or better. The stages and/or actuators can be of the locking type, so as to prevent errant position adjustments once the system has been properly aligned. Once the "optics bracket assembly", including the attached mirror or mirror stack, is attached to the flexural pivots, the mirror or mirror stack can be rotated freely about the flexural pivot axes, and thus about the X-ray tube focal spot, without causing any degradation in the optical alignment.

Precise, controlled rotation of the "optics bracket assembly" about the focal spot is achieved using a linear motor drive or a linear translation stage (210), which is arranged in a sine-bar configuration: the linear drive or stage pushes against one edge of the optics bracket assembly, via an intermediate drive plate (211) and drive post (212), thereby causing rotation of the mirror (106) or mirror stack (108) about the focal spot (102) in the counter-clockwise direction when viewed from the right side. The flexural pivots or bearings, complemented by a simple spring (217), provide the restoring torque needed to rotate the optics bracket assembly in the clockwise direction when the linear drive is retracted. The precision of this design is more than sufficient: for example, using a translation stage with 1 micron resolution, positioned to push against the optics bracket assembly a distance of 80 mm from the rotation axis, an angular resolution of better than 0.001 degrees will be achieved.

Figure 4:
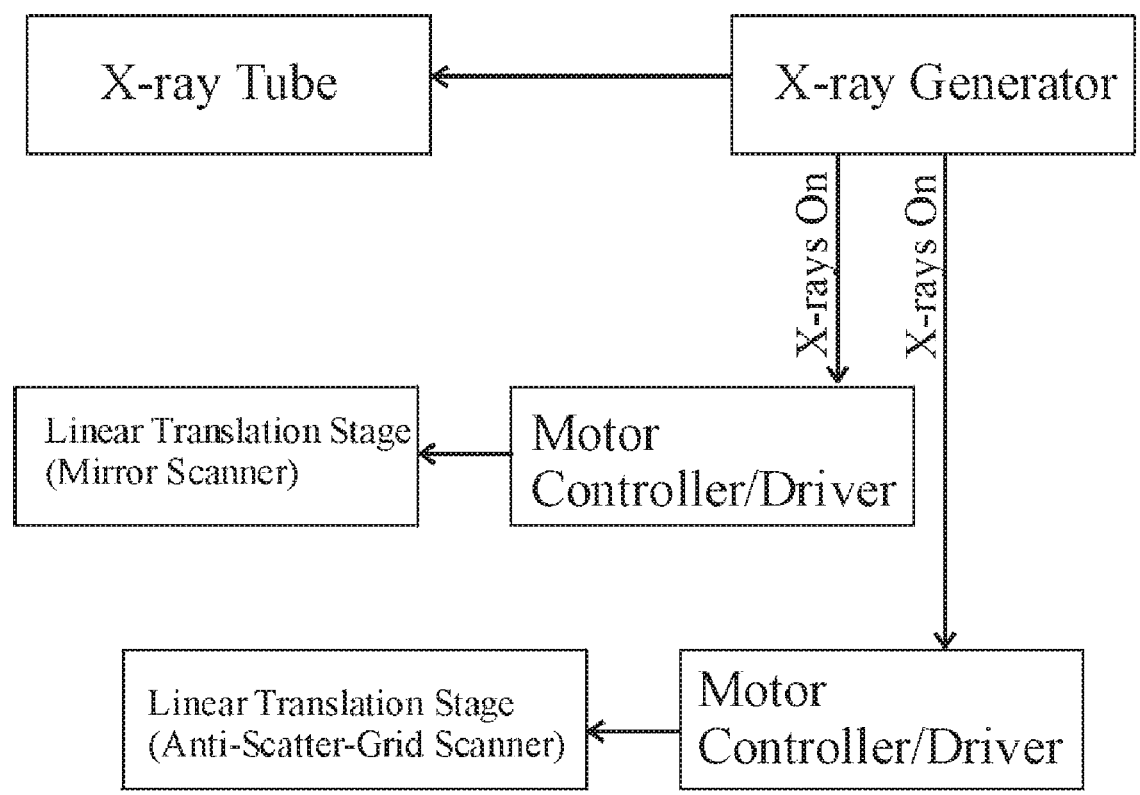
FIG. 4 is a block diagram showing how the mirror scan drive, and optionally the anti-scatter-grid scan drive, is synchronized with the X-ray generator, in accordance with the invention.

As shown in the block diagram of FIG. 4, the linear motor drive or linear translation stage used to rotate the X-ray mirror or mirrors is activated by an electronic motor controller/driver that is synchronized with the X-ray generator to ensure that the mirrors move in such a way so as to provide the desired X-ray illumination pattern in the image plane during an X-ray exposure. For example, in the case of a full-field exposure using a single X-ray mirror, the mirror scan starts and stops when the X-ray exposure begins and ends, respectively; the extent of the mirror rotation (i.e., the start and end points) is determined by the desired exposure field in the image plane. The mirror rotation rate can be held constant over the entire exposure, to provide an illumination pattern comparable to that which would be obtained without using any mirrors (i.e., monotonically decreasing intensity along one direction, due to the heel effect), or the rotation rate can be modulated to produce whatever arbitrary illumination pattern is desired (e.g., more or less sharply decreasing intensity along one direction, non-monotonic intensity decrease, etc.) for optimal imaging, depending on the imaging task. For example, in a mammographic application, the mirror rotation rate may be set to a slow speed when scanning over a region adjacent the torso and increase as scanning approaches the nipple (greater intensity is typically required for thicker portions of tissue). Similar synchronization and illumination flexibility also can be obtained with a mirror stack in place of a single mirror.

In the case of a system incorporating a stack of X-ray mirrors, by controlling the design of the multilayer coatings on each mirror in the stack, the individual reflected fan beams can all be tuned to the same X-ray energy, or individual mirrors can be tuned to different X-ray energies. That is, all the mirrors can be coated with identical multilayers all tuned to a single X-ray energy, or alternatively the stack may include sets of mirrors, with each mirror set tuned to a specific X-ray energy. By constructing mirror stacks from sets of mirrors tuned to specific X-ray energies, and by providing a mechanism for selecting specific mirror sets within the stack, the system provides a method for the X-ray technician to discretely 'tune' the energy so as to optimize the X-ray exposure for the given imaging task. Additionally, multi-energy mirror arrays enable the possibility of dual- (or multi-) energy imaging techniques, such as dual-energy contrast-enhanced imaging utilizing a contrast agent, for example.

Figure 5A:
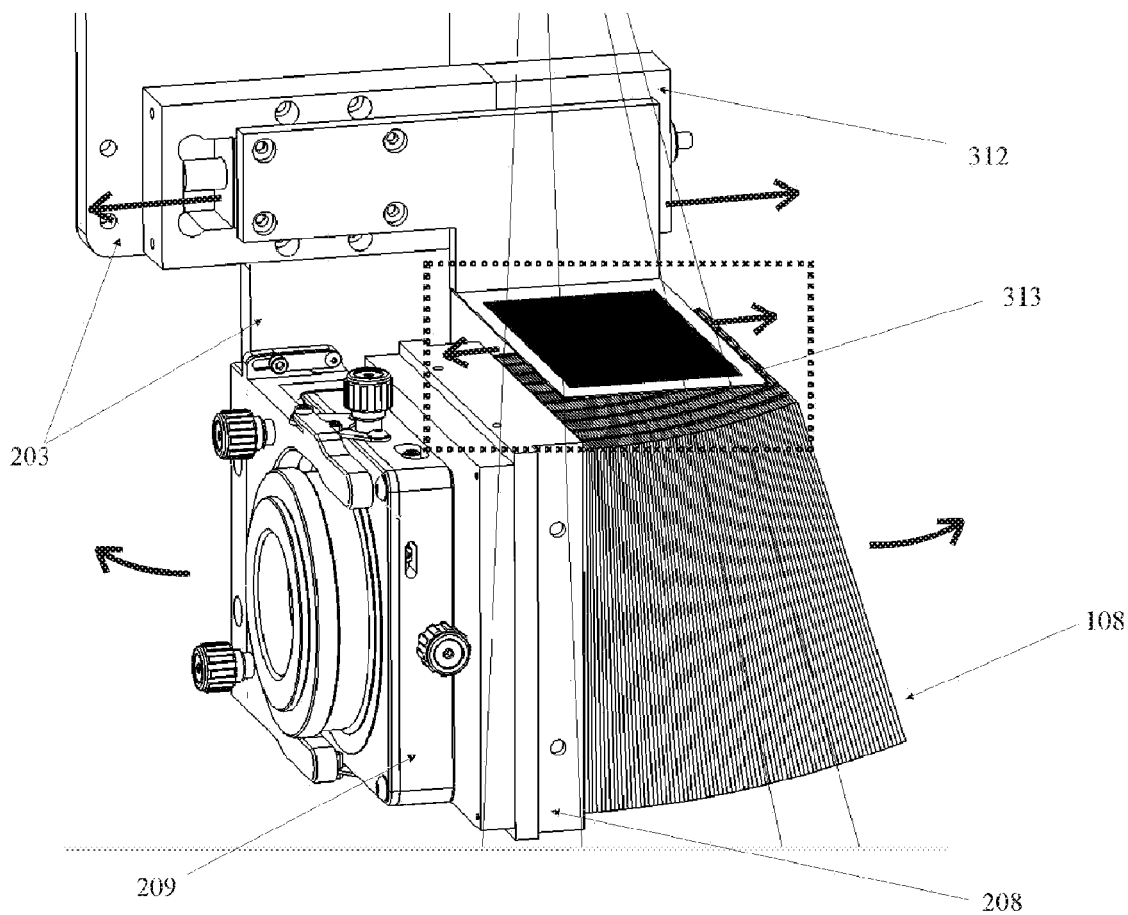
FIG. 5 is a cut-away view of a scanning optics bracket assembly in accordance with the invention, highlighting the scanning attenuation plate entrance grid.
Figure 5B:
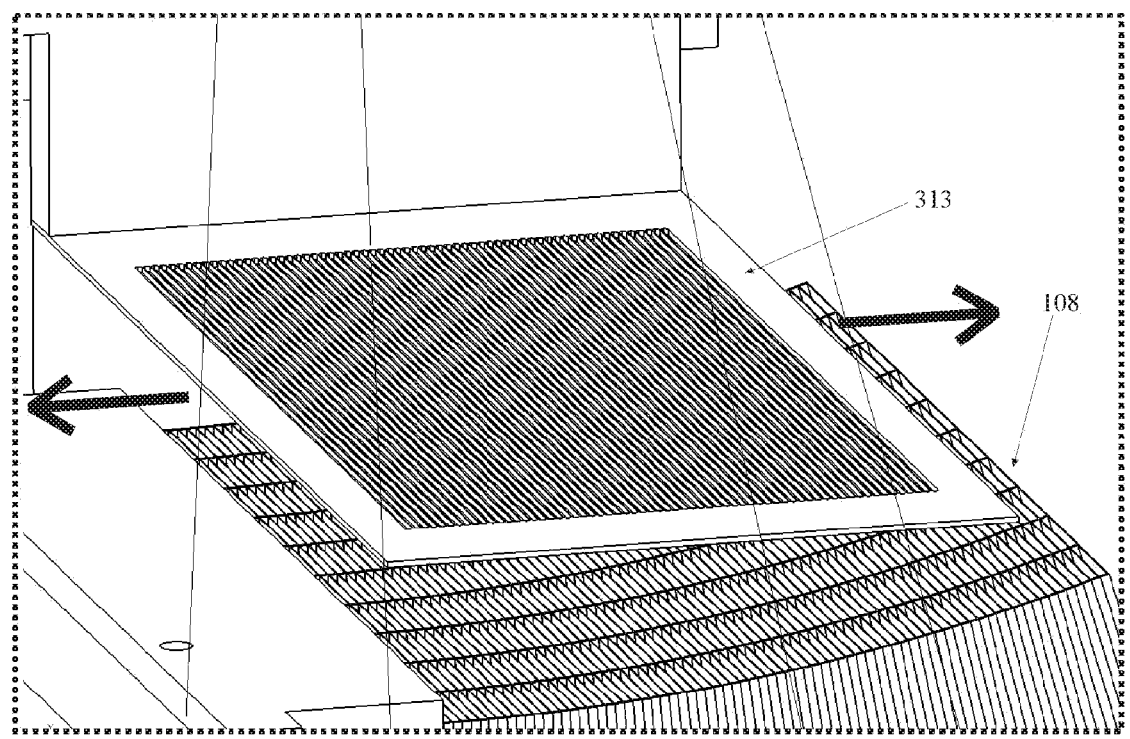

The present invention includes a mechanism for selecting a specific mirror set for use during an exposure that includes an X-ray attenuating plate or similar structure which is precisely positioned relative to the mirror stack. The attenuation plate is matched to the specific arrangement of mirrors in the mirror stack, and is designed to allow only certain mirrors to reflect and filter the X-ray beam. Adjustment of the position of the attenuation plate thereby provides a mechanism for discrete 'tuning' of the X-ray energy to the specific imaging task at hand. FIG. 5 shows a translatable X-ray attenuation plate for selecting specific mirrors in a mirror stack, including a linear translation stage (312) and a thin metal plate (313) into which the desired grid pattern or window has been formed. The metal grid can be fabricated using either conventional machining or chemical etching. One preferred embodiment utilizes a grid made of a machined brass plate of order 1 to 2 mm in thickness. In another preferred embodiment, the grid is made of tantalum sheet of order 0.5 mm in thickness, that has been lithographically patterned and then chemically etched (see, for example, Fotofab, 3758 W. Belmont Ave., Chicago, Ill. 60618.) The grid is rigidly attached to the translation stage; the translation stage is mounted to the optics bracket left-side plate (203). In the embodiment shown in FIG. 5, the entire stage/grid assembly is thus fixed in space relative to the X-ray mirror stack (108), i.e., between the X-ray tube and the mirror stack (108). Plate (313) here serves as an entrance grid to prevent X-rays from striking certain portions of the mirror stack while allowing X-rays to strike other portions of the mirror stack. As another option, attenuation plate (313) may be placed "downstream" of mirror stack (108) and thereby block X-rays of certain energies that are reflected off of the mirror stack from reaching the item to be imaged. In either configuration (between the X-ray tube and the mirror stack, or between the mirror stack and the to-be-imaged item), the relative position of the grid and the mirror stack is unchanged when the mirror stack is scanned using the sine-bar drive mechanism described above.

Figure 6A:
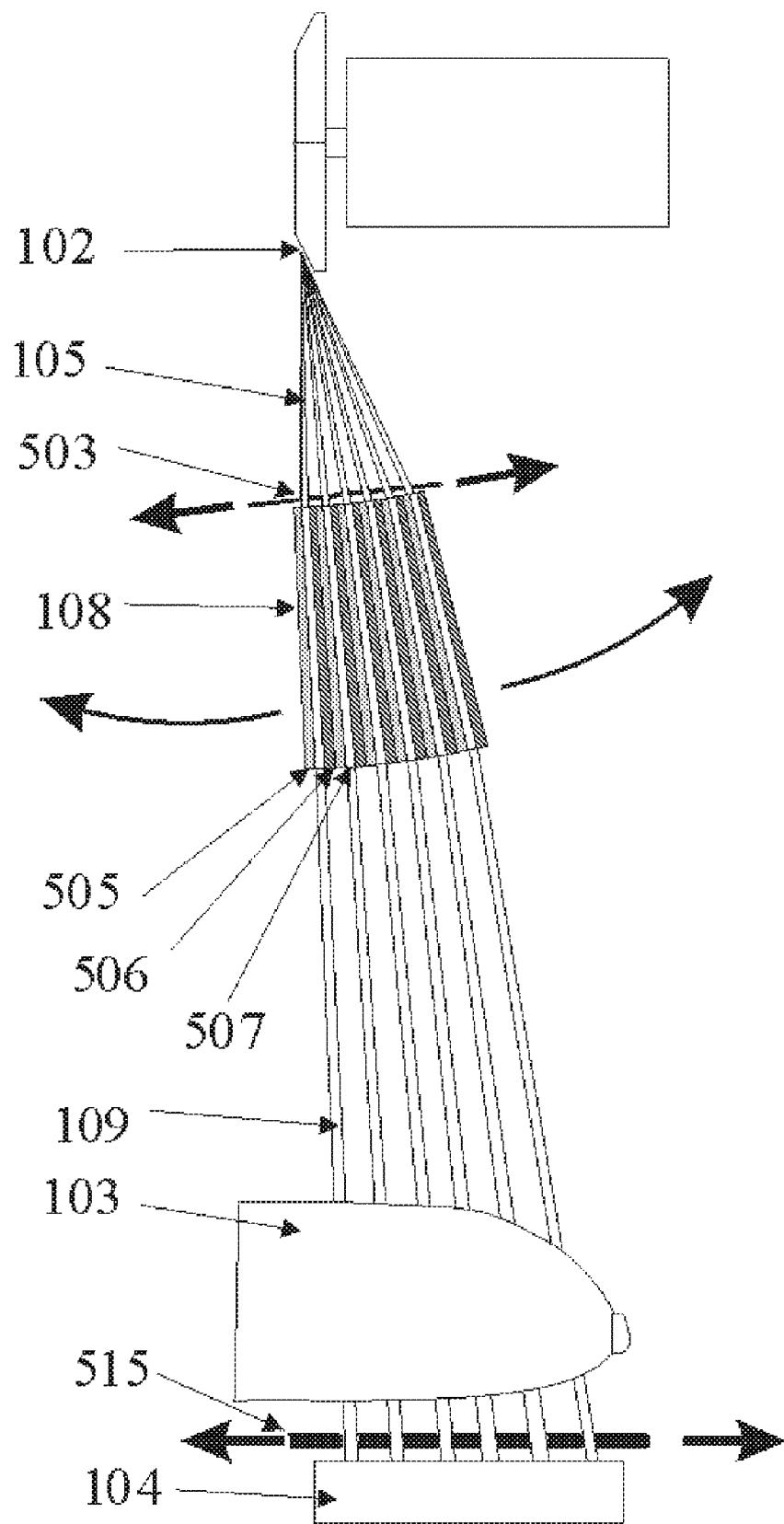
FIG. 6a shows a system with a mirror stack having three alternating mirror types, each tuned to a different X-ray energy.
Figure 6B:
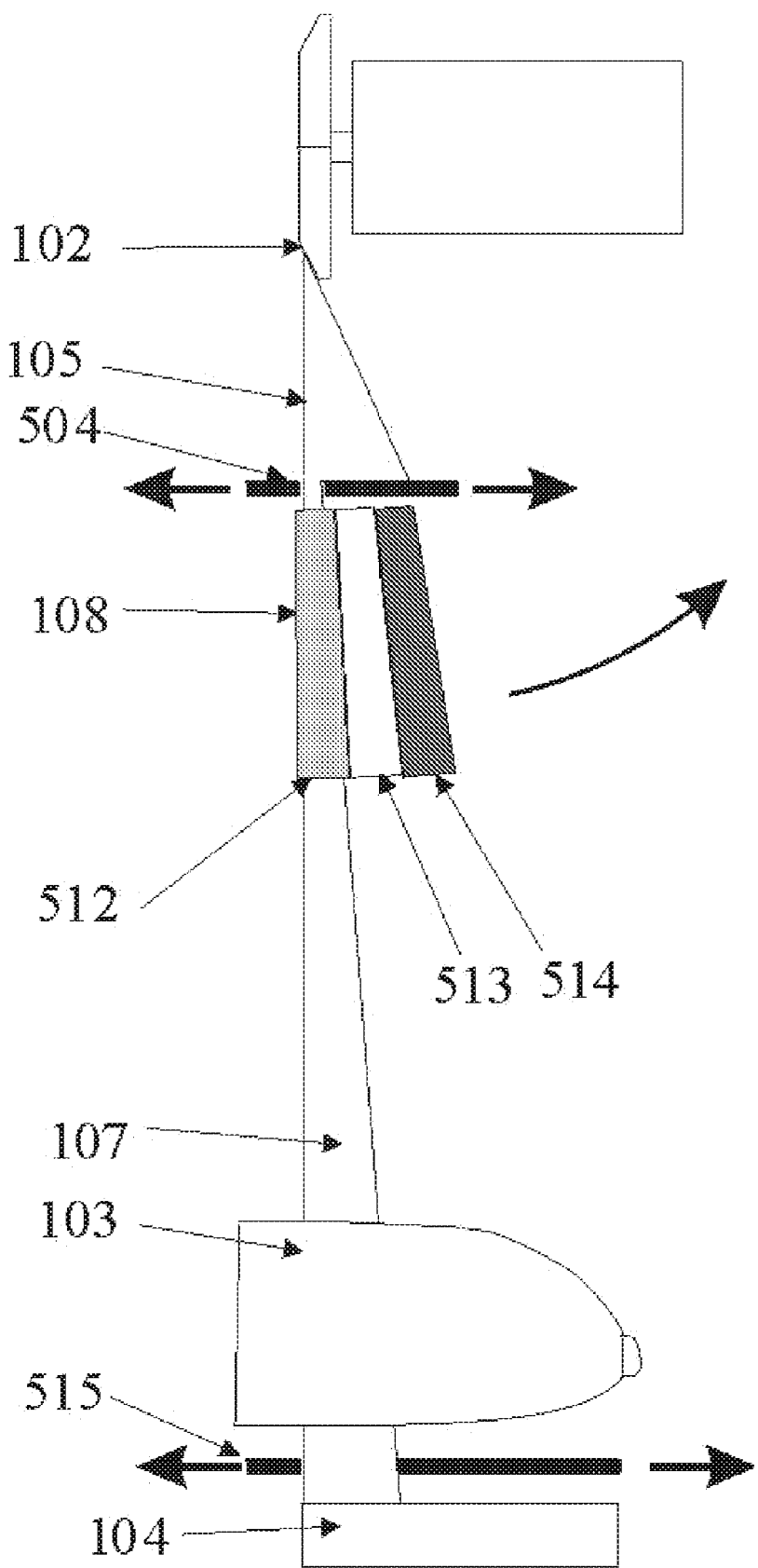
FIG. 6b shows a system with a mirror stack having three mirror types arranged in blocks.
Figure 7A:
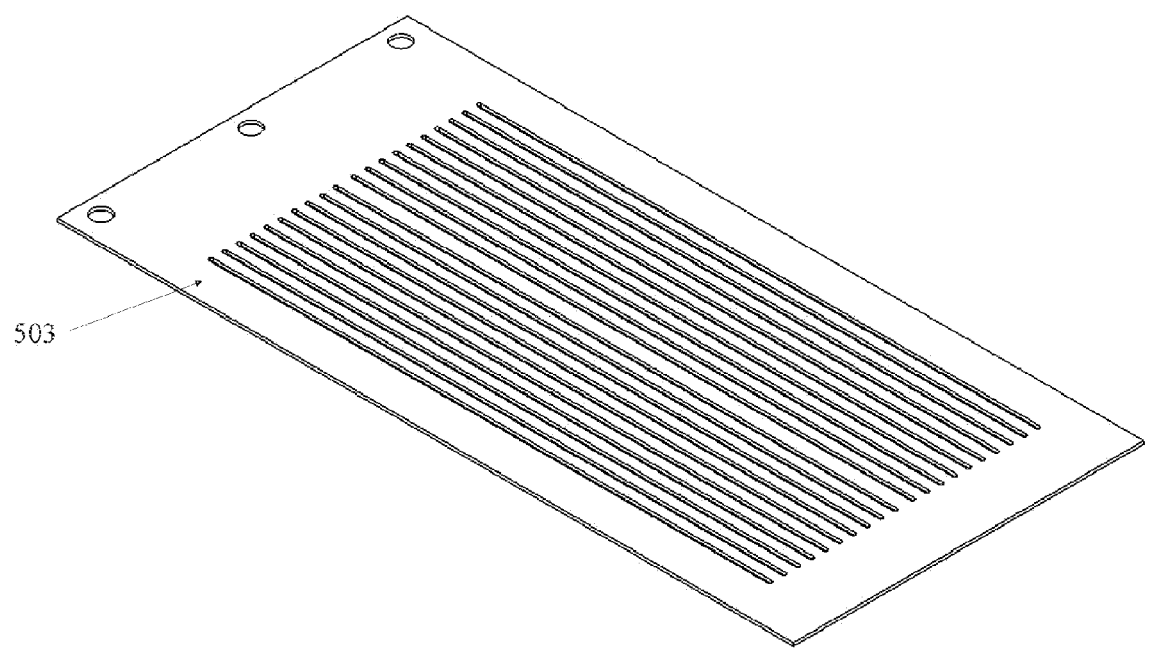
FIG. 7 shows example entrance grids in accordance with the invention. The embodiment of FIG. 7a is for use with the 3-energy alternating mirror stack shown in FIG. 6a, while the embodiment of FIG. 7b is for use with the 3-energy block mirror stack shown in FIG. 6b.
Figure 7B:
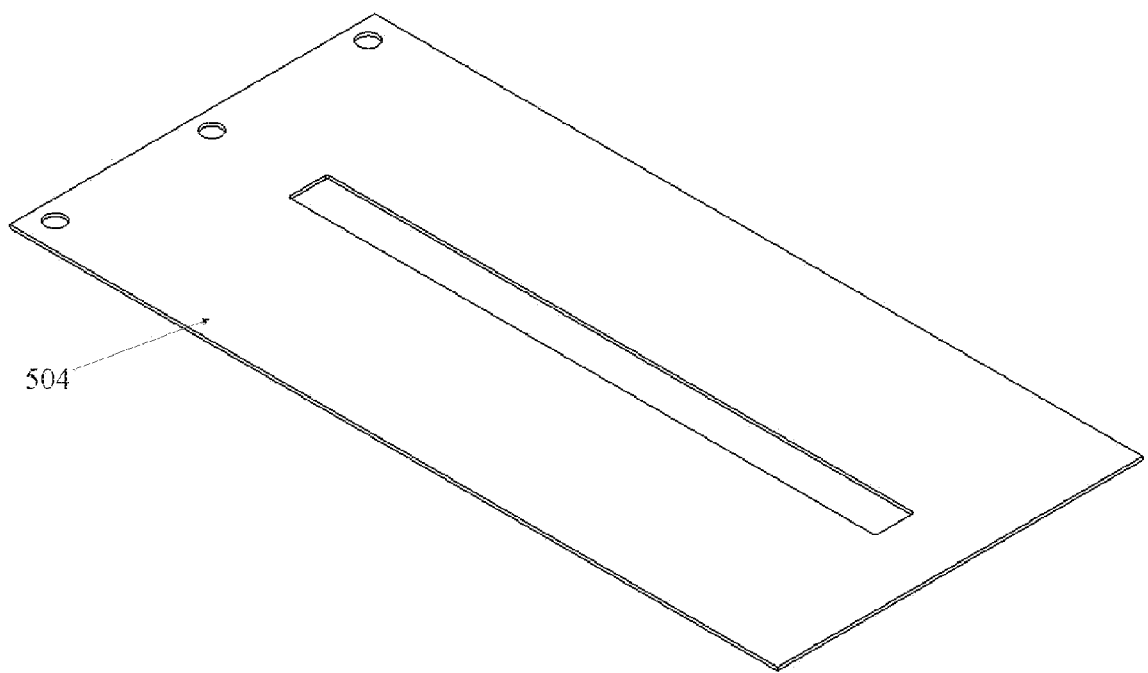

Shown in FIGS. 6 and 7 are two examples of multi-energy mirror stacks (FIG. 6) and the corresponding scanning attenuation plate (best seen in FIG. 7) used to select the mirror set for a given exposure. Both examples of attenuation plates in FIGS. 6 and 7 are "upstream" of the mirror stack as entrance grids; they could just as easily be disposed "downstream" of the mirror stack as exit grids. FIG. 6a shows an arrangement of three different mirror types (505, 506, 507), i.e., each tuned to some specific energy (e.g., 18 keV, 20 keV, and 25 keV), arranged in an alternating configuration, i.e., 505/506/507/505/506/507.... The entrance grid (503) appropriate for such a mirror arrangement is shown in FIG. 7a. Shown in FIG. 6b is another possible mirror-stack arrangement: in this case, three types of mirrors (512, 513, 514) are grouped together in blocks; the entrance grid (504) for this configuration is shown in FIG. 7b. Many other configurations are possible, using two or more different types of mirrors, with a large number of possible permutations of mirror ordering. In any case, by enabling the selection of substantially mono-energetic X-rays, image contrast is greatly improved while reducing patient dose (in clinical applications).

As described above, the X-ray mirrors used to produce mono-energetic X-rays yield a narrow fan beam, or a co-aligned array of narrow fan beams in the case of a stacked array of mirrors. The resultant illumination pattern in the image plane is a single bright strip in the case of a single mirror, or an array of bright strips in the case of a mirror array. The 'dark' areas in the image plane therefore can be masked during exposure, using an attenuating slotted plate exactly matched to the illumination pattern, which acts as an anti-scatter grid in order to minimize scattering along one direction. The anti-scatter grid would be scanned synchronously with the scanning of the mirrors during the exposure.

The final component of the present invention is a scanning anti-scatter grid as just outlined. Unlike conventional anti-scatter grids, this invention includes a grid that is exactly matched to the illumination pattern in the image plane produced by one or more X-ray mirrors. For example, in the case of a single-mirror that produces a narrow fan beam which is scanned over the image plane during X-ray exposure, the anti-scatter grid has a single slot whose width is exactly equal to the width of the bright strip of X-ray light produced in the image plane. As the mirror is scanned during exposure, the anti-scatter grid is scanned in synchronization (as shown in the block diagram of FIG. 4), thereby preventing X-ray light scattered by the sample or tissue from reaching areas of the X-ray detector outside of the envelope of the fan beam. In the case of a mirror array, the anti-scatter grid includes a set of parallel slots; the width of each slot is equal to the width of each individual bright X-ray strip in the image plane. Again, the anti-scatter grid is scanned in synchronization with the mirror array during exposure. Anti-scatter grids can also be used with multi-energy mirror array configurations, such as those shown in FIG. 6. Example scanning anti-scatter grids (515) matched to the two example types of 3-energy mirror stacks are shown in FIG. 6.

One preferred embodiment utilizes an anti-scatter grid made of a machined brass plate of order 1 to 2 mm in thickness. In another preferred embodiment, the grid is made of tantalum sheet of order 0.5 mm in thickness, that has been lithographically patterned and then chemically etched.

In operation, the invention works as follows. Prior to use in a clinical environment, the system must be aligned. The scanning axis of the minor or mirror stack must be properly aligned with the focal spot of the X-ray tube, using horizontal and vertical translation stages (305) and (307). The position of the mirror/stack must be properly aligned with the scanning axis, using the 5-axis optic positioner; this adjustment can be achieved through manual manipulation of threaded translation elements or with varying degrees of automation and computer control (e.g., a keyboard, joystick, or track ball, or other similar devices). Additionally, a visible light source registration system (not shown) must also be aligned with the X-ray mirror or mirror stack, so that an operator can easily determine where she is aiming the X-rays from the mirror/stack. A conventional visible light alignment system may be employed, or a visible light alignment system may be employed as described in co-pending and commonly owned and invented U.S. patent application Ser. No. 12/360,928, filed Jan. 28, 2009 and entitled "Optical Alignment System and Alignment Method for Radiographic X-Ray Imaging", now U.S. Pat. No. 7,794,144, the teachings of which are incorporated by reference herein. Again, these alignments are all performed by a service technician prior to clinical use the clinical technician should never adjust either the minor alignment or the scanner alignment.

In any event, there will be provided a visual indicator for the operator to know where the X-rays will strike the patient or the item to be imaged. Depending on the imaging task at hand, the operator selects one or more X-ray energies to transmit to the item to be imaged. By making such selection, attenuating entrance or exit grid (503, 504) on plate (313) is moved via linear translation stage (312) so that grid (503, 504) is aligned with the proper mirror or set of mirrors (512, 513, 514).

The X-ray tube is activated, causing linear translation stage (210) to push against the optics bracket assembly (203, 204, 205), thereby causing rotation about flexural pivots (213). Rotation of the assembly about the pivots causes the X-ray mirror/stack to scan. Travelling synchronously with the scanning mirror is anti-scatter grid (515) to minimize scattering. The scanning speed of the mirror/stack can be adjusted; the slower the scanning speed, the greater the intensity of the X-rays transmitted to the item to be imaged.

The invention is not limited to the above description. For example, while multiple mirrors each tuned to the same X-ray energy may be provided in blocks or as interspersed sets within a mirror stack, the invention is not so limited; a single mirror (or more than one) may be provided for each desired X-ray energy. Further, these respective mirrors each tuned to different X-ray energies may be provided within a common mirror stack, or they need not be, or they may be individually mounted each on its own mirror mount.

Having described certain embodiments of the invention, it should be understood that the invention is not limited to the above description or the attached exemplary drawings. Rather, the scope of the invention is defined by the claims appearing hereinbelow and any equivalents thereof as would be appreciated by one of ordinary skill in the art.

What is claimed is:

1. A multilayer X-ray mirror alignment and scanning system for X-ray imaging devices utilizing an X-ray point-source having a focal spot, comprising:
    a multi-axis adjustable mirror mount upon which at least one multilayer X-ray mirror is mounted, said multilayer X-ray mirror comprising i) a substrate distinct from said mirror mount, and ii) a multilayer X-ray reflective coating disposed on said substrate, said mirror mount pivotable about a scanning axis alignable with the focal spot; and
    a computer-controlled mirror scanner, coupled with said mirror mount and synchronized in operation with the X-ray point-source so that an activation time of said mirror scanner is synchronized with an activation time of the X-ray point source,
    wherein when the X-ray point-source is operated, said mirror scanner moves said mirror mount about said scanning axis.

2. An alignment and scanning system for X-ray imaging devices according to claim 1, said mirror mount being attached to an optics bracket pivotably mounted with respect to the focal spot.

3. An alignment and scanning system for X-ray imaging devices according to claim 2, said mirror scanner comprising a linear motor drive applying force against said optics bracket and causing said optics bracket and said mirror mount to rotate about said scanning axis but remain aligned with the focal spot.

4. An alignment and scanning system for X-ray imaging devices according to claim 1, said mirror mount further comprising a 5-axis optic positioner having three orthogonal translations and two orthogonal rotations, adapted to enable positioning of the mirror relative to the focal spot and said scanning axis.

5. An alignment and scanning system for X-ray imaging devices according to claim 1, further comprising a two-axis adjustment mechanism adapted to position said scanning axis of said mirror mount relative to the X-ray focal spot.

6. An alignment and scanning system for X-ray imaging devices according to claim 1, said at least one multilayer X-ray mirror comprising a plurality of multilayer mirrors rigidly secured to one another in a mirror stack.

7. An alignment and scanning system for X-ray imaging devices according to claim 6, said mirror stack further comprising at least a first plurality of multilayer mirrors adapted to reflect X-rays of a first energy and a second plurality of multilayer mirrors adapted to reflect X-rays of a second energy.

8. An alignment and scanning system for X-ray imaging devices according to claim 7, further comprising a movable radiopaque plate having at least one slot dimensioned to correspond to at least one but not all of said pluralities of multilayer mirrors, disposed either one of i) interposed between the X-ray point-source and said mirror stack, or ii) interposed between said mirror stack and the item to be imaged, said slot selectively allowing at least one of said pluralities of multilayer mirrors to transmit X-rays of at least one corresponding energy to the item to be imaged and said radiopaque plate blocking at least another of said pluralities of mirrors from transmitting X-rays of at least one different corresponding energy.

9. An alignment and scanning system for X-ray imaging devices according to claim 8, said first plurality of mirrors being substantially all adjacent one another in a first block and said second plurality of mirrors being substantially all adjacent one another in a second block, wherein said slot comprises an aperture correspondingly dimensioned to substantially match one of said blocks to allow X-rays to be transmitted by one of said blocks while said radiopaque plate shields the other of said blocks.

10. An alignment and scanning system for X-ray imaging devices according to claim 8, said first and second pluralities of mirrors being interspersed with one another, wherein said slot comprises a plurality of slots correspondingly dimensioned to substantially match one of said pluralities of mirrors to allow X-rays to be transmitted by at least one of said pluralities of mirrors while said radiopaque plate shields at least another of said pluralities of mirrors.

11. An alignment and scanning system for X-ray imaging devices according to claim 1, further comprising a scanning anti-scatter grid, disposed between an item to be imaged and an X-ray sensor, having an attenuating slotted plate matched to an illumination pattern created by said at least one X-ray mirror.

12. An alignment and scanning system for X-ray imaging devices according to claim 1, said mirror scanner operable at a selectively variable speed to thereby enable selective control of the scanning speed of said mirror.

13. An X-ray imaging device, comprising:
    an X-ray point-source having a focal spot;
    at least one multilayer X-ray mirror comprising i) a substrate, and ii) a multilayer X-ray reflective coating disposed on said substrate;
    a multi-axis adjustable mirror mount, distinct from said mirror substrate, upon which said at least one multilayer X-ray mirror is mounted, said mirror mount pivotable about a scanning axis alignable with said focal spot; and
    a computer-controlled mirror scanner, coupled with said mirror mount and synchronized in operation with said X-ray point-source so that the activation time of said mirror scanner is synchronized with the activation time of the X-ray point-source,
    wherein when said X-ray point-source is operated, said mirror scanner moves said mirror mount about said scanning axis.

14. An X-ray imaging device according to claim 13, said mirror scanner comprising a linear motor drive applying force against said mirror mount to rotate said mirror mount about said scanning axis but remain aligned with said X-ray focal spot.

15. An X-ray imaging device according to claim 13, said at least one multilayer X-ray mirror comprising a plurality of multilayer mirrors rigidly secured to one another in a mirror stack.

16. An X-ray imaging device according to claim 15, said mirror stack further comprising at least a first plurality of multilayer mirrors adapted to reflect X-rays of a first energy and a second plurality of multilayer mirrors adapted to reflect X-rays of a second energy.

17. An X-ray imaging device according to claim 16, further comprising a movable radiopaque plate having at least one slot dimensioned to correspond to at least one but not all of said pluralities of multilayer mirrors, disposed either one of i) interposed between said X-ray point-source and said mirror stack, or ii) interposed between said mirror stack and the item to be imaged, said slot selectively allowing at least one of said pluralities of multilayer mirrors to transmit X-rays of at least one corresponding energy to the item to be imaged and said radiopaque plate blocking at least another of said pluralities of multilayer mirrors from transmitting X-rays of at least one different corresponding energy.

18. An X-ray imaging device according to claim 17, said first plurality of mirrors being substantially all adjacent one another in a first block and said second plurality of mirrors being substantially all adjacent one another in a second block, wherein said slot comprises an aperture correspondingly dimensioned to substantially match one of said blocks of multilayer mirrors to allow X-rays to be transmitted by at least one of said blocks while said radiopaque plate shields at least another of said blocks.

19. An X-ray imaging device according to claim 17, said first and second pluralities of mirrors being interspersed with one another, wherein said slot comprises a plurality of slots correspondingly dimensioned to substantially match one of said pluralities of multilayer mirrors to allow X-rays to be transmitted by at least one of said pluralities of mirrors while said radiopaque plate shields at least another of said pluralities of mirrors.

20. An X-ray imaging device according to claim 13, said mirror scanner operable at a selectively variable speed to thereby enable selective control of the scanning speed of said mirror.

21. An X-ray imaging device, comprising:
an X-ray point-source having a focal spot;
a plurality of multilayer X-ray mirrors, each of said multilayer mirrors comprising i) a substrate and ii) a multilayer X-ray reflective coating disposed on said substrate, in communication with said X-ray point-source, including at least a first multilayer mirror adapted to reflect X-rays of a first energy and a second multilayer mirror adapted to reflect X-rays of a second energy;
a scannable mirror mount distinct from said substrates upon which said plurality of multilayer mirrors are mounted, said mirror mount alignable with said focal spot; and
a movable radiopaque plate having at least one slot dimensioned to correspond to at least one but not all of said multilayer mirrors, disposed either one of i) interposed between the X-ray point-source and said multilayer mirrors, or ii) interposed between said multilayer mirrors and the item to be imaged, said slot selectively allowing at least one of said multilayer mirrors to transmit X-rays of at least one corresponding energy to the item to be imaged and said radiopaque plate blocking at least another of said mirrors from transmitting X-rays of at least one different corresponding energy, thereby selecting an X-ray energy to be transmitted for imaging.

22. An X-ray imaging device according to claim 21, said plurality of multilayer mirrors being rigidly secured to one another in a minor stack, said first multilayer minor further comprising a first plurality of multilayer minors, and said second multilayer minor further comprising a second plurality of multilayer minors, said first plurality of multilayer mirrors being substantially all adjacent one another in a first block and said second plurality of multilayer mirrors being substantially all adjacent one another in a second block, wherein said slot comprises an aperture correspondingly dimensioned to substantially match one of said blocks to allow X-rays to be transmitted by at least one of said blocks while said radiopaque plate shields at least another of said blocks.

23. An X-ray imaging device according to claim 21, said plurality of multilayer mirrors being rigidly secured to one another in a minor stack, said first multilayer minor further comprising a first plurality of multilayer minors, and said second multilayer minor further comprising a second plurality of multilayer minors, said first and second pluralities of multilayer minors being interspersed with one another, wherein said slot comprises a plurality of slots correspondingly dimensioned to substantially match one of said pluralities of multilayer mirrors to allow X-rays to be transmitted by at least one of said pluralities of mirrors while said radiopaque plate shields at least another of said pluralities of multilayer mirrors.

24. An X-ray imaging device according to claim 21, said minor mount pivotable about a scanning axis alignable with said focal spot, said X-ray imaging device further comprising a computer-controlled minor scanner, coupled with said minor mount and synchronized in operation with said X-ray point-source so that an activation time of said mirror scanner is synchronized with an activation time of the X-ray point source,
wherein when said X-ray point-source is operated, said minor scanner moves said minor mount about said scanning axis.

25. An X-ray imaging device according to claim 24, said mirror scanner operable at a selectively variable speed to thereby enable selective control of the scanning speed of said minor.

26. An X-ray imaging device, comprising:
an X-ray point-source having a focal spot;
a plurality of multilayer X-ray mirrors, in communication with said X-ray point source, including at least a first multilayer mirror comprising i) a first substrate and ii) a first multilayer X-ray reflective coating disposed on said first substrate, adapted to reflect X-rays of a first energy and a second multilayer minor comprising i) a second substrate and ii) a second multilayer X-ray reflective coating disposed on said second substrate, adapted to reflect X-rays of a second energy;
a first scanable minor mount distinct from said first substrate upon which said first minor is mounted, said first minor mount alignable with said focal spot;
a second scanable mirror mount distinct from said second substrate upon which said second minor is mounted, said second minor mount alignable with said focal spot and
a movable radiopaque plate having at least one slot dimensioned to correspond to one of said first or second multilayer mirrors, disposed either one of i) interposed between the X-ray point-source and said multilayer minors, or ii) interposed between said multilayer minors and the item to be imaged, said slot selectively allowing one of said first or second multilayer minors to transmit X-rays of a corresponding energy to the item to be imaged and said radiopaque plate blocking the other of said first or second multilayer mirrors from transmitting X-rays of at least one different corresponding energy, thereby selecting an X-ray energy to be transmitted for imaging.

27. A method of performing X-ray imaging utilizing substantially mono-energetic X-rays, comprising the steps of:
providing a plurality of multilayer X-ray minors including at least a first multilayer minor having i) a first substrate and ii) a first multilayer X-ray reflective coating disposed on the first substrate adapted to reflect X-rays of a first energy and a second multilayer mirror having i) a second substrate and ii) a second multilayer X-ray reflective coating disposed on the second substrate adapted to reflect X-rays of a second energy; and selectively allowing X-rays from an X-ray source to be transmitted by at least one of the mirrors while blocking X-rays from at least another of the mirrors, thereby selecting an X-ray energy to be transmitted for imaging, said selectively allowing step further comprising the steps of:

providing a movable radiopaque plate having at least one slot dimensioned to correspond to one of said multilayer mirrors either between the X-ray source and the minors or between the mirrors and an item to be imaged; and selectively moving the radiopaque plate so as to align the slot with desired one(s) of the X-ray mirrors.

28. A method of performing substantially mono-energetic X-ray imaging according to claim 27, further comprising the steps of:

mounting the mirrors on a mirror mount distinct from the first or second substrates and pivotable about a scanning axis alignable with a focal spot of the X-ray source; and rotating the minor mount about the scanning axis while maintaining alignment of the scanning axis with the X-ray focal spot.

29. A method of performing substantially mono-energetic X-ray imaging according to claim 28, further comprising the step of varying the speed of rotation of the minor mount about the scanning axis to thereby enable selective control of the scanning speed of said minors.

30. A method of performing substantially mono-energetic X-ray imaging according to claim 29, further comprising the steps of utilizing said speed varying step and said radiopaque plate moving step to control X-ray intensity and energy, respectively, as a function of position with respect to an item to be imaged.

31. An alignment and scanning system for X-ray imaging devices according to claim 13, further comprising a scanning anti-scatter grid, disposed between an item to be imaged and an X-ray sensor, having an attenuating slotted plate matched to an illumination pattern created by said at least one multilayer X-ray mirror.

32. An alignment and scanning system for X-ray imaging devices according to claim 21, further comprising a scanning anti-scatter grid, disposed between an item to be imaged and an X-ray sensor, having an attenuating slotted plate matched to an illumination pattern created by said plurality of multilayer X-ray mirrors.

33. An alignment and scanning system for X-ray imaging devices according to claim 26, further comprising a scanning anti-scatter grid, disposed between an item to be imaged and an X-ray sensor, having an attenuating slotted plate matched to an illumination pattern created by at least one of said first or second multilayer X-ray mirrors.

* * * * *